US007112716B2

(12) United States Patent
Ausubel et al.

(10) Patent No.: US 7,112,716 B2
(45) Date of Patent: Sep. 26, 2006

(54) METHODS FOR SCREENING AND IDENTIFYING HOST PATHOGEN DEFENSE GENES

(75) Inventors: Frederick M. Ausubel, Newton, MA (US); Rhonda Feinbaum, Arlington, MA (US); Man Wah Tan, Palo Alto, CA (US); Geneviève Alloing, Nice (FR); Dennis Kim, Belmont, MA (US)

(73) Assignee: The General Hospital Corporation, Boston, MA (US)

( * ) Notice: Subject to any disclaimer, the term of this patent is extended or adjusted under 35 U.S.C. 154(b) by 356 days.

(21) Appl. No.: 10/042,066

(22) Filed: Oct. 18, 2001

(65) Prior Publication Data

US 2002/0194624 A1    Dec. 19, 2002

Related U.S. Application Data

(63) Continuation-in-part of application No. 09/827,789, filed on Apr. 6, 2001, now abandoned.

(60) Provisional application No. 60/195,097, filed on Apr. 6, 2000.

(51) Int. Cl.
*A01K 67/033* (2006.01)
(52) U.S. Cl. .............................. 800/8; 800/9; 424/9.1; 424/9.2
(58) Field of Classification Search ............. 800/3, 800/8, 9; 424/9.1, 9.2
See application file for complete search history.

(56) References Cited

U.S. PATENT DOCUMENTS

| 4,713,378 | A | 12/1987 | Perrone et al. ............ 514/192 |
|---|---|---|---|
| 5,270,448 | A | 12/1993 | Payne ............................ 514/2 |
| 5,366,995 | A | 11/1994 | Savage et al. ............. 514/558 |
| 5,853,998 | A | 12/1998 | Ohno et al. ................... 435/6 |

FOREIGN PATENT DOCUMENTS

| WO | WO 94/16077 | 7/1994 |
|---|---|---|
| WO | WO 95/11969 | 5/1995 |
| WO | WO 96/30053 | 10/1997 |
| WO | WO 97/38714 | 10/1997 |
| WO | WO 97/38722 | 10/1997 |
| WO | WO 97/39011 | 10/1997 |
| WO | WO 97/39017 | 10/1997 |
| WO | WO 98/12205 | 3/1998 |
| WO | EP 0 843 011 | 5/1998 |
| WO | EP 0 843 014 | 5/1998 |
| WO | EP 0 843 016 | 5/1998 |
| WO | WO 98/20157 | 5/1998 |
| WO | WO 98/50080 | 11/1998 |
| WO | WO 98/50554 | 11/1998 |
| WO | WO 99/18996 | 4/1999 |

OTHER PUBLICATIONS

Garrington et al. Current Opinion in Cell Biology, 1999, 11: 211-218.*
Aballay et al., "Programmed Cell Death Mediated by ced-3 and ced-4 Protects Caenorhabditis elegans from Salmonella typhimurium-Mediated Killing," Proc. Nat. Acad. Sci. 98:2735-2739 (2001).
Aballay et al., "Salmonella typhimurium Proliferates and Establishes a Persistent Infection in the Intestine of Caenorhabditis elegans," Current Biology 10:1539-1542 (2000).
Alexander et al., "Surgical Infections and Choice of Antibiotics" Surgical Infections, 13:221-236 W.B. Saunders (ed) Philadelphia, PA (1991).
Bent et al., "RPS2 of Arabidopsis thaliana: A Leucine-Rich Repeat Class of Plant Disease Resistance Genes," Science 265:1856-1860 (1994).
Berka and Vasil, "Phospholipase C (Heat-Labile Hemolysin) of Pseudomonas aeruginosa: Purification and Preliminary Characterization," Journal of Bacteriology 152:239-245 (1982).
Bestwick et al., "Localization of Hydrogen Peroxide Accumulation during the Hypersensitive Reaction of Lettuce Cells to Pseudomonas syringae pv phaseolicola," The Plant Cell 9:209-221 (1997).
Bloch et al., "Pathogenicity Island Evaluation in Escherichia coli K1 by Crossing with Laboratory Strain K-12," Infection and Immunity 64:3218-3223 (1996).
Blum et al., "Gene Clusters Encoding the Cytotoxic Necrotizing Factor Type 1, Prs-fimbriae and α Hemolysin form the Pathogenicity Island II of the Uropathogenic Escherichia coli Strain J96," FEMS Microbiology Letters 126:189-195 (1995).
Bucher. "Pathogens of Tobacco and Tomato Hornworms," Journal of Invertebrate Pathology 9:82-89 (1967).
Bulla et al., "Bacteria as Insect Pathogens ," Annu. Rev. Microb. 29:163-190 (1975).
Caparon et al., "Genetic Manipulation of Pathogenic Streptococci," Methods In Enzymology 204:556-586 (1991).
Carniel et al., "Characterization of a Large Chromosomal "High-Pathogenicity Island" in Biotype 1B Yersinia enterocolitica,"Journal of Bacteriology 178:6743-6751 (1996).
Censini et al., "cag, A Pathogenicity Island of Helicobacter pylori, Encodes Type I-Specific and Disease-Associated Virulence Factors," Proc. Natl. Acad. Sci. USA 93:14648-14653 (1996).
Chadwick et al., "Adherence Patterns and Virulence for Galleria mellonella Larvae of Isolates of Serratia marcescens," Journal of Invertebrate Pathology 55:133-134 (1990).
Chadwick et al., "Serological Responses of Insects," Federation Proceedings 26:1675-1679 (1967).
Charpentier et al., "The Bacterial Flora of the Midgut of Two Danish Populations of Healthy Fifth Instar Larvae of the Turnip Moth, Scotia segetum," Journal of Invertebrate Pathology 32:59-63 (1978).

(Continued)

Primary Examiner—Scott D. Priebe
(74) Attorney, Agent, or Firm—Clark & Elbing LLP (57) ABSTRACT

Disclosed are methods for identifying nematodes having enhanced susceptibility to a pathogen; for identifying pathogen defense response genes; and for identifying compounds that enhances a host's defense response to a pathogen.

20 Claims, 4 Drawing Sheets

OTHER PUBLICATIONS

Cho et al., "Ornamental Plants as Carriers of *Pseudomonas aeruginosa,*" *Phytopathology* 65:425-431 (1975).

Cohn et al., "The Effect of Amiloride on Pigment Expression in a Clinical Isolate of *Pseudomonas Aeruginosa,*" *Current Therapeutic Research* 51:562-567 (1992).

Conrad et al., "Efficacy of Aztreonam in the Treatment of Skeletal Infections Due to *Pseudomonas aeruginosa,*" *Review of Infectious Research* 13:S634-S639 (1991).

Darby et al., "Lethal paralysis of *Caenorhabditis elegans* by Pseudomonas *aeruginosa,*" *Proc. Nat. Acad. Sci.* 96:15202-15207 (1999).

Debener et al., "Indentification and molecular mapping of a single *Arabidopsis thaliana* locus determining resistance to a phytopathogenic *Pseudomonas syringae* isolate, " *The Plant Journal* 1:289-302 (1991).

Dong et al., "Induction of *Arabidopsis* Defense Genes by Virulent and Avirulent *Pseudomonas* syringae Strains and by a Cloned Avirulence Gene," *The Plant Cell* 3:61-72 (1991).

Dunny et al., "Pheromone-Inducible Conjugation in *Enterococcus faecalis*: Interbacterial and Host-Parasite Chemical Communication," *Journal Of Bacteriology* 177:871-876 (1995).

Dunphy et al., "Octopamine, a Modulator of the Haemocytic Nodulation Response of Non-immune *Galleria mellonella* Larvae," *J. Insect. Physiol.* 40:267-272 (1994).

Dunphy, " Interaction of mutants of *Xenorhabdus nematophilus* (*Enterobacteriaceae*) with antibacterial systems of *Galleria mellonella* larvae (Insecta: Pyralidae)," *Can. J. Microbiol.* 40:161-168 (1994).

Elrod et al., "A Phytopathogenic Bacterium Fatal to Laboratory Animals," *Science* 94:520-521 (1941).

Elrod et al., "*Pseudomonas Aeruginosa*; Its Role As Plant Pathogen," *Journal of Bacteriology* 46:633-645 (1942).

Fenselau et al., "Determinants of Pathogenicity in *Xanthomonas campestris pv. vesicatoria* are Related to Proteins Involved in Secretion in Bacterial Pathogens of Animals," *Molecular Plant-Microbe Interactions* 5:390-396 (1992).

Finlay et al., "Common Themes in Microbial Pathogenicity Revisited," *Microbiology and Molecular Biology Reviews* 61:136-169 (1997).

Fuqua et al., "Quorum Sensing in Bacteria: the LuxR-LuxI Family of Cell Density-Responsive Transcriptional Regulators," *Journal of Bacteriology* 176:269-275 (1994).

Geels, "*Pseudomonas tolaaasii* Control by Kasugamycin in Cultivated Mushrooms (*Agaricus bisporus,*)" *Journal of Applied Bacteriology* 79:38-42 (1995).

Gingrich, "Acquired Humoral Immune Response of the Large Milkweed Bug, *Oncopeltus Fasciatus* (Dallas), To Injected Materials," *J. Ins. Physiol.* 10:179-194 (1964).

Glazebrook et al., "Isolation of Arabidopsis Mutants with Enhanced Disease Susceptibility by Direct Screening," *Genetics* 143:973-982 (1996).

Gough et al., "*hrp* Genes of *Pseudomonas solanacearum* are Homologous to Pathogenicity Determinants of Animal Pathogenic Bacteria and are Conserved Among Plant Pathogenic Bacteria," *Molecular Plant-Microbe Interactions* 5:384-389 (1992).

Green et al., "Agricultural Plants and Soil as a Reservoir for *Pseudomonas aeruginosa,*" *Applied Microbiology* 28:987-991 (1974).

Grewal et al., "Effects of Bacteria Isolated from a Saprophagous Rhabditid Nematode *Caenorhabditis Elegans* on the Mycelial growth of *Agaricus bisporus,*" *J. Applied Bacteriology* 72:173-179 (1992).

Groisman et al., "How *Salmonella* became Pathogen," *Trends Microbiol.* 5:343-349 (1997).

Groisman et al., "Pathogenicity Islands: Bacerial Evolution in Quantum Leaps," *Cell* 87;791-794 (1996).

Hacker et al., "Pathogenicity Islands of Virulent Bacteria: Structure, Function and Impact on Microbial Evolution," *Molecular Microbiology* 23:1089-1097 (1997).

Harshey et al., "Spinning tails: Homologies among Bacterial Flagellar Systems," *Trends in Microbiology* 4:226-231 (1996).

Hoffmann et al., "Insect Immunity: *Galleria Mellonella* And Other Lepidoptera Have Cecropia-P9-Like Factors Active Against Gram Negative Bacteria," *Insect Biochem* 11:537-548 (1981).

Holloway, "Genetic Recombination in *Pseudomonas aeruginosa,*" *J. Gen. Microbiol.* 13:572-581 (1955).

Huang et al., "Characterization of the *Pseudomonas syringae* pv. *syringae* 61 *hrpJ* and *hrpI* Genes: Homology of HrpI to a Superfamily of Proteins Associated with Protein Translocation," *Molecular Plant-Microbe Interactions* 6:515-520 (1993).

Huang et al., "The *Pseudomonas syringae* pv. syringae 61 *hrpH* Product, an Envelope Protein Required for Elicitation of the Hypersensitive Response in Plants," *Journal of Bacteriology* 174:6878-6885 (1992).

Iglewski et al., "NAD-Dependent Inhibition of Protein Synthesis by *Pseudomonas aeruginosa* Toxin," *Proc. Nat. Acad. Sci. USA* 72:2284-2288 (1975).

Ike et al., "Genetic Analysis of the pAD1 Hemolysin/Bacteriocin Determinant in *Enterococcus faecalis*: Tn917 Insertional Mutagenesis and Cloning," *J. Bacteriol.* 172:155-163, (1990).

Ishimoto et al., "Formation of Pilin in *Pseudomonas aeruginosa* Requires the Alternative σ factor (RpoN) of RNA Polymerase," *Proc. Nat. Acad. Sci. USA* 86:1954-1957 (1989).

Jarosz, "Interaction of *Pseudomonas aeruginosa* proteinase with the Inducible Non-Self Response System of Insects," *Cytobios* 83:71-84 (1995).

Jett et al., "Virulence of Enterococci." *Clin. Microbiol. Rev.* 7:462-478 (1994).

Johnston et al., "Transcriptional Activation of *Salmonella typhimurium* Invasion Genes by a Member of the Phosphorylated Response-Regulator Superfamily," *Molecular Microbiology* 22:715-727 (1996).

Kamon et al., "Immune Response of Locusts to Venom of the Scorpion," *Journal of Invertebrate Pathology* 7:192-198 (1965).

Kanost et al., "Isolation and Characterization of a Hemocyte Aggregation Inhibitor From Hemolymph of *Manduca sexta* Larvae," *Archives of Insect Biochemistry and Physiology* 27:123-136 (1994).

Kaska, "The Toxicity of Extracellular Proteases of the Bacterium *Serratia marcescens* for Larvae of Greater Wax Moth, *Galleria mellonella,* " *Journal of Invertebrate Pathology* 27:271 (1976).

Kominos et al., "Introduction of *Pseudomonas aeruginosa* into a Hospital via Vegetables," *Applied Microbiology* 24:567-570 (1972).

Kovach et al., "A Putative Integrase Gene Defines the Distal End of a Large Cluster of ToxR-Regulated Colonization Genes in *Vibrio cholerae,*" *Microbiol.* 142:2165-2174 (1996).

Kovalchik et al., "*Neisseria gonorrhoeae*: Colonial Morphology of Rectal Isolates," *Applied Microbiology* 23:986-989 (1972).

Kunkel et al., "*RPS2*, an Arabidopsis Disease Resistance Locus Specifying Recognition of *Pseudomonas syringae* Strains Expressing the Avirulence Gene *avrRpt2,*" *The Plant Cell* 5:865-875 (1993).

Labrousse et al., "*Caenorhabditis elegans* is a Model Host for *Salmonella typhimurium,*" *Current Biol.* 10:1543-1545 (2000).

Laville et al., "Global Control in *Pseudomonas fluorescens* Mediating Antibiotic Synthesis and Suppression of Black Root Rot of Tobacco," *Proc. Natl. Acad. Sci. USA* 89:1562-1566 (1992).

Lee, "Pathogenicity Islands and the Evolution of Bacterial Pathogens," *Infectious Agents and Dis.* 5:1-7 (1996).

Lee, "Type III Secretion Systems: Machines to Deliver Bacterial Proteins into Eukaryotic Cells?," *Trends Microbiol.* 5:148-156 (1997).

Lemaitre et al., "The Dorsoventral Regulatory Gene Cassette *spätzle/Toll/cactus* Controls the Potent Antifungal Response in Drosophila Adults," *Cell* 86:973-983 (1996).

Leonard et al., "*Enterococcus faecalis* pheromone Binding Protein, PrgZ, Recruits a Chromosomal Oligopeptide Permease System to Import Sex Pheromone cCF10 for Induction of Conjugation," *Proc. Natl Acad. Sci. USA* 93:260-264 (1996).

Lysenko, "*Pseudomonas*-An Attempt at a General Classification," *J. Gen. Microbiol.* 25:379-408 (1961).

Lysenko, "The Mechanisms of Pathogenicity of *Pseudomonas aeruginosa* (Schroeter) Migula I. The Pathogenicity of Strain N-06 for Larvae of the Greater Wax Moth, *Galleria mellonella* (Linnaeus)," *Journal of Insect Pathology* 5:78-82 (1963).

Lysenko, "The Mechanisms of Pathogenicity of *Pseudomonas aeruginosa* (Schroeter) Migula II. A Toxic Substance Produced in Filtrates of Cultures," *Journal of Insect Pathology* 5:83-88 (1963).

Lysenko, "The Mechanisms of Pathogenicity of *Pseudomonas aeruginosa* (Schroeter) Migula III. The Effect of N-06 Toxin on the Oxygen Consumption of *Galleria Prepupae*," *Journal of Insect Pathology* 5:89-93 (1963).

Lysenko, "The Mechanisms of Pathogenicity of *Pseudomonas aeruginosa* (Schroeter) Migula IV. The Antigenic Character of the Toxin Produced by Strain N-06," *Journal of Insect Pathology* 5:94-97 (1963).

Lysenko, "Chitinase of Serratia marcescens and Its Toxicity to Insects," *J. of Invertebrate Patho.* 27:385-386 (1976).

Mahairas et al., "Molecular Analysis of Genetic Differences between *Mycobacterium bovis* BCG and Virulent M. *bovis*," *J. of Bacteriol.* 178:1274-1282 (1996).

Mahajan-Miklos et al., "Molecular Mechanisms of Bacterial Virulence Elucidated Using a *Pseudomonas aeruginosa-Caenorhabditis elegans* Pathogenesis Model," *Cell* 96:47-56 (1999).

Marschalek et al., "Transfer RNA Genes: Landmarks for Integration of Mobile Genetic Elements in *Dictyostelium discoideum*," *Science* 244:1493-1496 (1989).

Mel et al., "Modulation of Horizontal Gene Transfer in Pathogenic Bacteria by In Vivo Signals," *Cell* 87:795-798 (1996).

Meyers et al., "Infections Caused by Microorganisms of the Genus *Erwinia*," *Annals of Internal Medicine* 76:9-14 (1972).

Mittler et al., "Inhibition of Programmed Cell Death in Tobacco Plants during a Pathogen-Induced Hypersensitive Response at Low Oxygen Pressure," *The Plant Cell* 8:1991-2001 (1996)

Moellering, "Emergence of Enterococcus as a Significant Pathogen," *Clinical Infectious Diseases* 14:1173-1178 (1992).

Molinari et al., "Inhibition of *Pseudomonas aeruginosa* Virulence Factors by Subinhibitory Concentrations of Azithromycin and Other Macrolide Antibiotics," *J. Antimicrob. Chemother.* 31:681-688 (1993).

Mullett et al., "Analysis of Immune Defences of the Wax Moth, *Galleria mellonella*, with Anti-haemocytic Monoclonal Antibodies," *J. Insect Physiol.* 39:897-902 (1993).

Murray, "The Life and Times of the Enterococcus," *Clinical Microbiology Reviews* 3:46-65 (1990).

Ochman et al., "Identification of a Pathogenicity Island required for *Salmonella* Survival in Host Cells," *Proc. Natl. Acad. Sci.* 93:7800-7804 (1996).

Ohman et al., "Toxin A-Deficient Mutants of *Pseudomonas aeruginosa* PA 103: Isolation and Characterization," *Infection and Immunity* 28:899-908 (1980).

Ostroff et al., "Identification of a New Phospholipase C Activity by Analysis of an Insertional Mutation in the Hemolytic Phospholipase C Structural Gene of *Pseudomonas aeruginosa*," *Journal of Bacteriology* 169:4597-4601 (1987).

Pant et al., "Cellulolytic Activity In A Phytophagous Lepidopteran Insect *Philosamia Ricini*: The Origin of the Enzymes," *Insect Biochem.*, 19:269-276 (1989).

Preston et al., "Rapid and Sensitive Method for Evaluating *Pseudomonas aeruginosa* Virulence Factors during Corneal Infections in Mice," *Infection and Immunity* 63:3497-3501 (1995).

Pye et al., "Hemocytes Containing Polyphenoloxidase in *Galleria Larvae* after Injections of Bacteria," *Journal of Invertebrate Pathology* 19:166-170 (1972).

Rahme et al., "Common Virulence Factors for Bacterial Pathogenicity in Plants and Animals," *Science* 268:1899-1902 (1995).

Rahme et al., "Use of Model Plant Hosts to Identify *Pseudomonas aeruginosa* Virulence Factors," *Proc. Natl. Acad. Sci. USA* 94:13245-13250 (1997).

Raun et al., "Bacterial Pathogens in Iowa Corn Insects," *Journal of Insect Pathology* 5:66-71 (1963).

Reimmann et al., "The Global Activator GacA of *Pseudomonas aeruginosa* PAO Positively Controls the Production of the Autoinducer N-butyryl-homoserine Lactone and the Formation of the Virulence Factors Pyocyanin, Cyanide, and Lipase," *Molecular Microbiology* 24:309-319 (1997).

Rich et al., "Genetic Evidence that the gacA Gene Encodes the Cognate Response Regulator for the *lemA* Sensor in *Pseudomonas syringae*," *Journal of Bacteriology* 176:7468-7475 (1994).

Ritter et al., "tRNA Genes and Pathogenicity Islands: Influence on Virulence and Metabolic Properties of Uropathogenic *Escherichia coli*," *Molecular Microbiology* 17:109-121 (1995).

Russell et al., "Antibacterial Proteins in the Midgut of *Manduca sexta* During Metamorphosis," *J. Insect Physiol.* 42:65-71 (1996).

Schroth et al., "Epidemiology of *Pseudomonas Aeruginosa* in Agricultural Areas," *Pseudomonas aeruginosa: Ecological Aspects and Patient Colonization*, pp. 1-29 (1977).

Shea et al., "Identification of a Virulence Locus Encoding a Second Type III Secretion System in *Salmonella typhimurium*," *Proc. Natl. Acad. Sci. USA* 93:2593-2597 (1996).

Som et al., "Isolation & Identification of *Pseudomonas aeruginosa* Pathogenic to Insect Larvae," *Indian Journal of Experimental Biology* 18:590-593 (1980).

Sorensen et al., "Phenazine Pigments in *Pseudomonas aeruginosa* Infection," In: *Pseudomonas* Aeruginosa as an Opportunistic Pathogen, Campa et al., eds., Plenum Press, New York, pp. 42-57 (1993).

Stephens et al., "Some Properties of an Immune Factor Isolated From The Blood Of Actively Immunized Wax Moth Larvae," *Canadian Journal of Microbiology* 8:719-725 (1962).

Stephens, "Bactericidal Activity Of The Blood Of Actively Immunized Wax Moth Larvae," *Canadian Journal of Microbiology* 8:491-499 (1962).

Stephens, "Immune Responses Of Some Insects To Some Bacterial Antigens," *Canadian Journal of Microbiology* 5:203-228 (1959).

Stevens et al., "A Quantitative Model of Invasive *Pseudomonas* Infection in Burn Injury," *Journal of Burn Care & Rehabilitation* 15:232-235 (1994).

Swenson et al., "Two Pathogenicity Islands in Uropathogenic *Escherichia coli* J96: Cosmid Cloning and Sample Sequencing," *Infection and Immunity* 64:3736-3743 (1996).

Swift et al., "Quorum Sensing: A Population-Density Component in the Determination of Bacterial Phenotype," *Trends Biochem. Sci.* 21:214-219 (1996).

Tan et al., "Killing of *Caenorhabditis elegans* by *Pseudomonas aeruginosa* Used to Model Mammalian Bacterial Pathogenesis," *Proc. Natl. Acad. Sci. USA* 96:715-720 (1999).

Tan et al., "*Pseudomonas aeruginosa* Killing of *Caenorhabditis elegans* used to Identify *P. aeruginosa* Virulence Factors," *Proc. Natl. Acad. Sci. USA* 96:2408-2413 (1999).

Trotter et al., "Mutants of *Enterococcus faecalis* Deficient as Recipients in Mating with Donors Carrying Pheromone-Inducible Plasmids," *Plasmid* 24:57-67 (1990).

Turner et al., "Occurrence, Biochemistry and Physiology of Phenazine Pigment Production," *Advances in Microbial Physiology* 27:210-275 (1986).

Vlayen et al., "Identification Of The Gut Bacterial Micro Flora In Armyworms Mamestra-Brassicae Lepidoptera Noctuidae Importance Of The Environment," *Annales de la Societe Royale Zoologique de Belgique* 112:23-39 (1982).

Webster's II, New Riverside University Dictionary, The Riverside Publishing Company. Definitions of "Mushroom" and "Fungus." pp. 512 and 778 (1988).

Winans et al., "Adaptation of a conjugal Transfer System for the Export of Pathogenic Macromolecules," *Trends In Microbiology* 64:64-68 (1996).

Xu et al., "Molecular Cloning of Genes that Specify Virulence in *Pseudomonas solanacearum*," *Journal of Bacteriology* 170:617-622 (1988).

Fire et al., "Potent and Specific Genetic Interference by Double-Stranded RNA in Caenorhabditis Elegans", *Nature*, 391:806-811 (1998).

Kurz et al., "Caenorhabditis Elegans for the Study of Host-Pathogen Interactions", *Trends in Microbiology*, 8:142-144 (2000).

Montgomery et al., "RNA as a Target of Double-Stranded RNA-Mediated Genetic Interference in Caenorhabditis Elegans", *Proc. Natl. Acad. Sci.*, 95:15502-15507 (1998).

Tan et al., "Caenorhabditis Elegans: a Model Genetic Host to Study Pseudomonas Aeruginosa Pathogenesis", *Current Opinion In Microbiology*, 3:29-34 (2000).

\* cited by examiner

Methods for Screening and Identifying Host Pathogen Defense Genes

METHODS FOR SCREENING AND IDENTIFYING HOST PATHOGEN DEFENSE GENES

CROSS-REFERENCE TO RELATED APPLICATIONS

This application is a continuation-in-part of U.S. application Ser. No. 09/827,789 filed on Apr. 6, 2001, now abandoned which in turn claims benefit of U.S. provisional application 60/195,097, filed on Apr. 6, 2000.

STATEMENT AS TO FEDERALLY SPONSORED RESEARCH

This invention was made, in part, with government funding. The Government therefore has certain rights in the invention.

BACKGROUND OF THE INVENTION

The invention relates to screening methods for identifying host pathogen defense genes and their regulating pathways, and for identifying drugs that enhance or stimulate the resistance of a host to pathogen infection or that block pathogen virulence.

Microbial pathogens use a variety of complex strategies to subvert host cellular functions to ensure their multiplication and survival. Some pathogens that have co-evolved or have had a long-standing association with their hosts utilize finely tuned host-specific strategies to establish a pathogenic relationship. During infection, pathogens encounter different conditions, and respond by expressing virulence factors that are appropriate for the particular environment, host, or both.

Although antibiotics have been effective tools in treating infectious disease, the emergence of drug resistant pathogens is becoming problematic in the clinical setting. New antibiotics or antipathogenic molecules are therefore needed to combat such drug resistant pathogens. Similarly, the discovery of drugs that maximize host pathogen defense responses is also warranted. Moreover, a need in the art exists for screening methods aimed at identifying and characterizing the host defense response, including the genes regulating the pathogen defense pathway that enable hosts to combat infecting pathogens.

SUMMARY OF THE INVENTION

In one aspect, the invention features a method for identifying a nematode having enhanced susceptibility to a pathogen. The method, in general, involves the steps of: (a) exposing a mutagenized nematode to a pathogen; and (b) determining survival of the mutagenized nematode when exposed to the pathogen, decreased survival of the mutagenized nematode relative to a non-mutagenized nematode identifying the mutagenized nematode as one having enhanced susceptibility to the pathogen. In preferred embodiments, the mutagenized nematode is *C. elegans* (such as an N2 L4 worm). In other preferred embodiments, the pathogen is a bacterium (such as *Pseudomonas aeruginosa* (strain PA14) or *Enterococcus faecalis*). In still other preferred embodiments, the mutagenized nematode is exposed to the pathogen under slow killing conditions. In yet another embodiment, the mutagenized nematode includes a mutation in a component of a MAPK signal transduction pathway (such as mutations in esp-2, esp-8, and pmk-1).

In another aspect, the invention features a method for identifying a pathogen defense response gene. The method, in general, involves the steps of: (a) exposing a mutagenized nematode to a pathogen; (b) determining survival of the mutagenized nematode when exposed to the pathogen, decreased survival of the mutagenized nematode relative to a non-mutagenized nematode indicating a mutation in a nematode pathogen defense response gene; and (c) using the mutation as a marker for identifying the pathogen defense response gene.

In another aspect, the invention features a method for identifying a nematode having enhanced susceptibility to a pathogen. The method, in general, involves the steps of: (a) providing a nematode including a double-stranded RNA (dsRNA), wherein the dsRNA silences the expression of an endogenous nematode gene; (b) exposing the nematode to a pathogen; and (c) determining survival of the nematode when exposed to the pathogen, decreased survival of the nematode having dsRNA relative to a control nematode identifying the nematode having dsRNA as one with enhanced susceptibility to the pathogen. In preferred embodiments, the nematode is *C. elegans* (e.g., an N2 L4 worm) and the dsRNA is microinjected into the nematode. In another embodiment, the nematode including the dsRNA results from the nematode ingesting dsRNA-expressing bacteria.

In other preferred embodiments, the pathogen is a bacterium (e.g., *Pseudomonas aeruginosa* (strain PA14) or *Enterococcus faecalis*). Preferably, the nematode is exposed to the pathogen under slow killing conditions.

In yet another aspect, the invention features a method for identifying a pathogen defense response gene. The method, in general, includes the steps of: (a) providing a nematode including a dsRNA, wherein the dsRNA silences an endogenous nematode gene; (b) exposing the nematode to a pathogen; (c) determining survival of the nematode when exposed to the pathogen, wherein decreased survival of the nematode having dsRNA relative to a control nematode indicates that the dsRNA silences a pathogen defense gene; and (d) determining the nucleic acid sequence of the dsRNA, thereby identifying the pathogen defense response gene. In preferred embodiments, the nucleic acid sequence of the dsRNA is known. In other preferred embodiments, the nematode is *C. elegans* (e.g., an N2 L4 worm). And in still other preferred embodiments, the dsRNA is microinjected into the nematode or results from a nematode ingesting dsRNA-expressing bacteria.

In other preferred embodiments, the pathogen is a bacterium (e.g., *Pseudomonas aeruginosa* (strain PA14) or *Enterococcus faecalis*). Preferably, the nematode is exposed to the pathogen under slow killing conditions. In yet another embodiment, the mutagenized nematode includes a mutation in a component of a MAPK signal transduction pathway (such as mutations in esp-2, esp-8, and pmk-1).

In yet another aspect, the invention features a method for identifying a component of a MAPK signal transduction pathway conferring innate immunity to a nematode. The method, in general, involves the steps of: (a) providing a nematode having a mutation in a component of a MAPK signal transduction pathway and a pathogen; and (b) determining survival of the nematode when exposed to the pathogen, decreased survival of the nematode relative to a wild type nematode identifying a component of the MAPK signal transduction pathway that confers innate immunity to a nematode. In preferred embodiments, the component of the MAPK signal transduction pathway is a gene encoding a MAPK (e.g., pmk-1), a gene encoding a MAPKK (e.g., esp-2); or a gene encoding a MAPKKK (e.g., esp-8).

In another aspect, the invention features a method for identifying a nematode having enhanced susceptibility to a pathogen, involving the steps of: (a) providing a nematode including a double-stranded RNA (dsRNA), wherein the dsRNA silences the expression of a component of a MAPK signal transduction pathway; (b) exposing the nematode to a pathogen; and (c) determining survival of the nematode when exposed to the pathogen, decreased survival of the nematode having dsRNA relative to a control nematode identifying the nematode having dsRNA as one with enhanced susceptibility to the pathogen. In preferred embodiments, the component of the MAPK signal transduction pathway is a gene encoding a MAPK; a gene encoding a MAPKK; or a gene encoding a MAPKKK.

In still another aspect, the invention features a method for identifying a compound that enhances a defense response to a pathogen. The method, in general, involves the steps of: (a) exposing a nematode, having enhanced pathogen susceptibility, to a test compound and a pathogen; and (b) determining survival of the nematode exposed to the pathogen, increased survival of the nematode relative to the survival of the nematode in the absence of the test compound identifying a compound that enhances a defense response to a pathogen.

In preferred embodiments, the nematode utilized in the compound screening assays is a mutagenized nematode identified according to the above-described method. In other preferred embodiments, the nematode includes dsRNA. Preferably, the test compound is provided in a compound library; is a small organic compound; or is a peptide, peptidomimetic, or an antibody or fragment thereof. In yet another embodiment, the mutagenized nematode includes a mutation in a component of a MAPK signal transduction pathway (such as mutations in esp-2, esp-8, and pmk-1).

In still other aspects, the invention features a method for identifying a compound that enhances a defense response to a pathogen, the method involving the steps of: (a) exposing a nematode, having a mutated MAPK signaling pathway, to a test compound and a pathogen; and (b) determining survival of the nematode exposed to the pathogen, increased survival of the nematode relative to the survival of the nematode in the absence of the test compound identifying a compound that enhances a defense response to a pathogen. In preferred embodiments, the component of the MAPK signal transduction pathway is a gene encoding a MAPK; a gene encoding a MAPKK, or a gene encoding a MAPKKK.

Exemplary pathogenic bacteria useful in the methods of the invention include, without limitation, *Aerobacter, Aeromonas, Acinetobacter, Agrobacterium, Bacillus, Bacteroides, Bartonella, Bordetella, Bortella, Borrelia, Brucella, Burkholderia, Calymmatobacterium, Campylobacter, Citrobacter, Clostridium, Cornyebacterium, Enterobacter, Enterococcus, Escherichia, Francisella, Gardnerella, Haemophilus, Hafnia, Helicobacter, Klebsiella, Legionella, Listeria, Morganella, Moraxella, Mycobacterium, Neisseria, Pasteurella, Proteus, Providencia, Pseudomonas, Salmonella, Serratia, Shigella, Staphylococcus, Streptococcus, Stentorophomonas, Treponema, Xanthomonas, Vibrio,* and *Yersinia.*

By "enhanced susceptibility to a pathogen" is meant that the genome of a host organism has been altered (e.g., by introducing a dsRNA molecule that silences an endogenous gene of a nematode) or mutated to render the host as having greater sensitivity to a pathogen than its unaltered or non-mutated counterpart. Typically, host organisms having enhanced susceptibility to a pathogen are preferably at least 5%, more preferably at least 25%, and most preferably at least 50% or more sensitive to the effects of a pathogen, when compared to a non-altered or non-mutated host organism.

By "inhibits a pathogen" is meant the ability of a test compound to decrease, suppress, attenuate, diminish, arrest, or stabilize the development or progression of a pathogen-mediated disease or infection in a eukaryotic host organism. Preferably, such inhibition decreases pathogenicity by at least 5%, more preferably by at least 25%, and most preferably by at least 50% or more, as compared to symptoms in the absence of the test compound in any appropriate pathogenicity assay (for example, those assays described herein). In one particular example, inhibition may be measured by monitoring pathogenic symptoms in a nematode infected with a pathogen exposed to a test compound or extract, a decrease in the level of pathogenic symptoms relative to the level of symptoms in the host organism not exposed to the compound indicating compound-mediated inhibition of the pathogen.

By "detectable marker" is meant a gene whose expression may be assayed; such genes include, without limitation, β-glucuronidase (GUS), luciferase (LUC), chloramphenicol transacetylase (CAT), green fluorescent protein (GFP), and β-galactosidase.

By "a component of a MAPK signaling pathway" is meant a polypeptide with identity to the mitogen-activated protein kinases (MAPK) or an polypeptide with identity to a MAPKK or MAPKKK. The core of a MAPK signaling pathway is composed of a MAP kinase (MAPK) (such as p38, JNKs, Jun amino-terminal kinases, or ERKs, extracellular signal-related kinases) whose activity is regulated via a MAPK-activating MAPK kinase (MAPKK) (such as MKK3/6, MKK4/7, or MEK1/2), which in turn is activated by a MAPKK-activating MAPKK kinase (MAPKKK) (such as ASK1 or c-Raf).

By "a mutated MAPK signaling pathway" is meant a MAPK signaling pathway having an alteration that enhances or diminishes a nematode innate immune response. Such an alteration might include without limitation the genetic inhibition of a MAPK (or a MAPKK or MAPKKK) by chemical or transposon-mediated mutagenesis, interference with MAPK gene expression by RNA-mediated interference, or the expression of a MAPK transgene, such a transgene might overexpress or interfere with a MAPK signaling component.

By "innate immunity" is meant a native or natural immunity whose defense mechanisms are present prior to exposure to infectious microbes or foreign substances.

The present invention provides a number of advantages. For example, the invention facilitates the identification of novel targets and therapeutic approaches for preparing therapeutic agents active on host factors and genes that enable a host to mount its defense against pathogen invasion and infection.

The invention also provides long awaited advantages over a wide variety of standard screening methods used for distinguishing and evaluating the efficacy of a compound against virtually any number of pathogens. In one particular example, the screening methods described herein allow for the simultaneous evaluation of host toxicity as well as anti-pathogenic potency in a simple in vivo screen. Moreover, the methods of the invention allow one to evaluate the ability of a compound to inhibit pathogenesis, and, at the same time, to evaluate the ability of the compound to stimulate and strengthen a host's response to pathogenic attack.

Accordingly, the methods of the invention provide a straightforward means to identify compounds that are both safe for use in eukaryotic host organisms (i.e., compounds which do not adversely affect the normal development and physiology of the organism) and efficacious against pathogenic microbes that establish infection and disease in their hosts. In addition, the methods of the invention provide a route for analyzing virtually any number of compounds for anti-pathogenic effect or for activating host defense pathways with high-volume throughput, high sensitivity, and low complexity. The methods are also relatively inexpensive to perform and enable the analysis of small quantities of active substances found in either purified or crude extract form. Furthermore, the methods disclosed herein provide a means for identifying compounds that have the capability of crossing eukaryotic cell membranes and which maintain therapeutic efficacy in an in vivo method of administration. In addition, the above-described methods of screening are suitable for both known and unknown compounds and compound libraries.

Other features and advantages of the invention will be apparent from the following description of the preferred embodiments thereof, and from the claims.

DETAILED DESCRIPTION OF THE INVENTION

The drawings will first be described.

Drawings

Below we describe experimental screens for identifying nematodes having enhanced resistance or susceptibility to the effects of pathogen invasion and infection. The screens and the nematodes described herein therefore provide a useful system for identifying novel host factors and genes responsible for a host's ability to combat infection, as well as for identifying compounds that either inhibit pathogenicity, promote a host's resistance to the pathogen, or both. The following experimental examples are intended to illustrate, not limit, the scope of the claimed invention.

Screen for *C. elegans* Mutants that are Resistant to Toxin-Mediated Killing by PA14

*C. elegans* fast-killing and slow-killing assays, respectively described in Mahajan-Miklos et al. (*Cell* 96:47–56, 1999) and Tan et al. (*Proc. Natl. Acad. Sci.* 96: L715–720, 1999), were used in genetic screens to identify host pathogen defense genes that are involved in the response to either toxin- or infection-mediated killing. Because the worms die rapidly and prior to producing progeny in the fast killing assay (FKA), it is an excellent assay for identifying mutants that are more resistant to toxin-mediated killing. A total of 10,000 ethylmethane sulfonate (EMS) mutagenized haploid genomes were screened for mutants that remained alive after 10 hours of exposure to *Pseudomonas aeruginosa* PA14 under fast killing conditions. Six mutants having resistance against *Pseudomonas* fast killing (designated rap mutants) were identified.

Screen for *C. elegans* Mutants with Enhanced Susceptibility to PA14

*C. elegans* mutants having enhanced susceptibility to pathogens (Esp) specifically PA14 under slow killing assay (SKA) conditions were identified using a standard F2 screen. The F2 screen was performed to identify recessive loss-of-function mutations in genes required for the *C. elegans* pathogen defense response. We recovered mutants that were more susceptible to PA14 because the infected worms die as gravid adults. After exposure to PA14, a dead worm containing its brood was transferred to plates seeded with *E. coli*, and its progeny were recovered.

N2 L4 worms were mutagenized with EMS according to standard procedures (Epstein and Shakes, eds., *Methods in Cell Biology*, Vol 48, *Caenorhabditis elegans*: Modern Biological Analysis of an Organism, Academic Press, 1995) and staged F2 progeny were then exposed to PA14 under SKA conditions. The plates were incubated overnight at 25° C., and 16–30 hours later screened for dead animals. Animals were determined to be dead when they no longer responded to touch by an eyelash. In control experiments, wild type N2 L4 worms began to die at 42 hours on PA14. Dead worms, many of which were bags containing hatched larvae, were then transferred to *E. coli* plates to recover their progeny.

Figure 1:
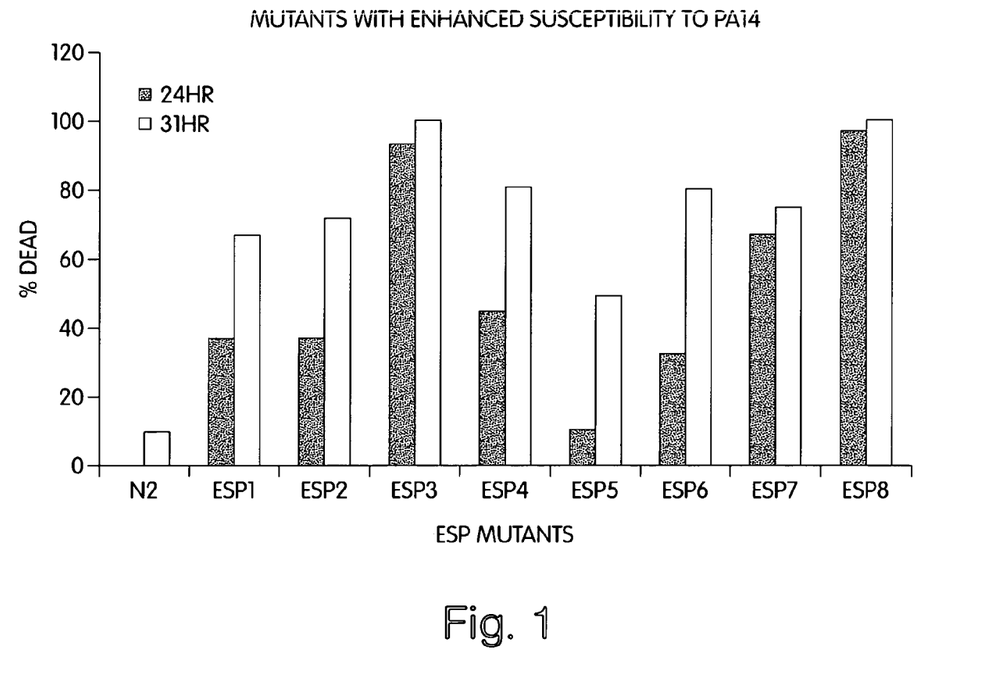
FIG. 1 shows a graph of several *C. elegans* mutants having enhanced susceptibility to PA14.

In two separate screens, a total of approximately 56,000 haploid genomes were examined for enhanced susceptibility to PA14. In one screen, from 42,000 mutagenized haploid genomes, 224 putative ESP mutants were identified. 132 worms produced no progeny, but of the remaining 92 mutants, 7 candidate Esp mutants were identified after two rounds of re-screening on PA14. Growth of the mutants was compared on PA14 and *E. coli* to establish that the apparent enhanced susceptibility to PA14 was not simply due to a shortened lifespan of the mutants. FIG. 1 shows the Esp phenotype of the mutants as isolated from the screen prior to backcrossing. All of the mutants showed some mortality after exposure to PA14 for only 24 hours (0% of N2 are dead at this time, the mutants range from 12–95% dead).

Characterization of *C. elegans* Esp Mutants

Genetic and phenotypic characterization of 8 putative Esp mutants was performed as follows. Seven of the eight mutants were backcrossed to N2 at least once. Standard backcrossing was performed by mating N2 males with each Esp mutant. Because it was not possible to distinguish self from cross progeny, matings were transferred daily and F1 hermaphrodites were selected only from mating plates with approximately 50% male progeny. F2 progeny of single F1's were then tested under SKA conditions for sensitivity to PA14. F2 worms that died 24–27 hours after exposure to PA14 were placed onto *E. coli* plates; and their F3 broods were subsequently tested for sensitivity to PA14. Only F2 animals yielding 100% susceptible progeny and that were derived from an F1 animal producing both wild type and susceptible progeny (ideally 1/4 susceptible progeny) were utilized as backcrossed strains.

While backcrossing the mutants to N2, F1 progeny were examined to determine whether the Esp mutations were recessive or X-linked or both. F1 hermaphrodite cross progeny (selected as described above) were tested directly under SKA conditions for sensitivity to PA14. At least 20 hermaphrodites were examined for each mutant tested. In all cases, the selected esp/+F1 hermaphrodites did not have an enhanced susceptibility to PA14, indicating that the Esp mutants were most likely recessive.

To determine whether the Esp mutation was X linked, F1 male progeny from the backcrosses were also examined.

Since all male progeny must contain only the X chromosome from the maternal parent (in this case the Esp mutant), X linkage is indicated if the F1 males show the Esp phenotype. Of the seven Esp mutants tested, three appear to be X linked (X linkage has been confirmed by mapping in the case of esp-1 and esp-2 but not for esp-3). Table 1 summarizes the characterization of several Esp mutants.

TABLE 1

Characterization of Esp Mutants

| Mutant | Gross Phenotype | Backcross | Recessive | Chromosomal location |
|---|---|---|---|---|
| esp-1 | Eat (thin, clear, reduced brood size) | 4X | Yes | X (−1.33 to 2.12) |
| esp-2 8-35-2 | Egl | 3X | Yes | X (−1.6 to −1.3) |
| esp-3 6-15 | | 2X | Yes | |
| esp-4 6-14 | | ND | ND | |
| esp-5 6-21 | | 1X | Yes | |
| esp-6 2-33 | Eat (thin) | 2 | Yes | |
| esp-7 7-9 | Eat (thin), Unc | 1X | Yes | |
| esp-8 8-17 | Egl | 2X | Yes | II −4.0 to −0.5 |

Characterization of esp-1

Figure 2:
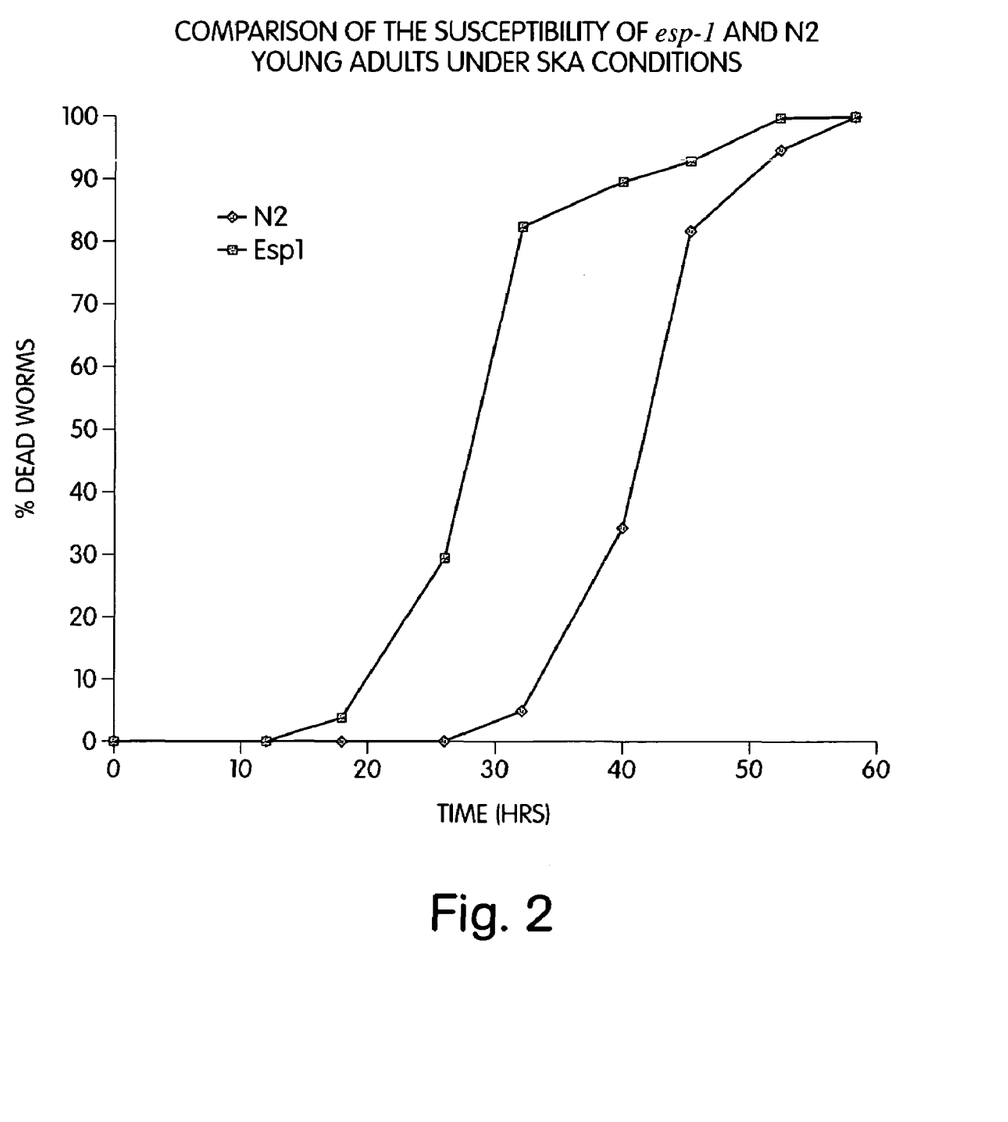
FIG. 2 is a graph showing a comparison of the susceptibility of esp-1 and N2 young adults under SKA conditions.

The mutant designated esp-1 was characterized according to standard methods. esp-1 young adults, under SKA conditions, were found to be significantly more susceptible to PA14 than wild type N2 worms (FIG. 2). In addition, esp-1 worms were found to be more sensitive to the bacterium *Enterococcus faecalis*. esp-1 worms also have an appearance associated with feeding defective mutants; they are thin, have a reduced brood size, and generally look partially starved (Avery, *Genetics* 133:897–917, 1993).

Mapping of esp-1

The esp-1 mutation was mapped to a 3.4 map unit interval on chromosome X by STS (sequence tags sites) mapping using the RW700 mapping strain (Williams, *Genetics* 131: 609–624 1992). RW700 is a strain of *C. elegans* that carries approximately 500 copies of the transposon TC1 scattered throughout the genome (the standard Bristol strain N2 has comparatively few TC1's). A set of TC1 insertions on each chromosome have been developed as STS markers and can be used to rapidly map a mutation to a genetic interval (Williams et al., *Genetics* 131: 609–624, 1992). Each STS marker can be detected by a unique PCR reaction; the presence of the STS marker indicates the RW7000 chromosome and the absence of the STS marker indicates that the sample is homozygous for the N2 chromosome. esp-1 males were crossed to RW700, and confirmed that the F2 were cross progeny as outlined above for backcrossing with N2.

To identify homozygous esp-1/esp-1 F2 animals from the RW7000 cross, F3 progeny from individual F2 animals were tested for their sensitivity to PA14. Only F2 animals producing 100% Esp F3 animals were selected as esp-1/esp-1 homozygotes suitable for mapping analysis. DNA for the PCR analysis was made from starved plates homozygous for the esp-1 mutation according to standard methods. In this manner, DNA from 150 F2 cross progeny homozygous for the esp-1 mutation were examined. STS mapping places esp-1 on chromosome X between markers stp33 and stp129 located at −1.33 and +2.12, respectively.

Using the available *C. elegans* genetic map and sequence data, the esp-1 interval was examined for genes known to mutate to an Esp or a feeding defective phenotype. Two such genes aex-2 and eat-13 are located in this interval (Thomas et al., Genetics 124: 855–872, 1990; Avery, *Genetics* 133: 897–917, 1993). A mutation in aex-2, which causes the worms to become constipated, has also been shown to confer an Esp phenotype. The sensitivity of aex-2(and other mutants defective in the expulsion step of defecation) to PA14 is presumably the result of their inability to expel PA14 accumulating in their guts. esp-1 does not have an obvious defecation phenotype and complements aex-2 for the Esp phenotype. eat-13 also maps within the genetic interval defined for esp-1. Like esp-1, eat-13 worms are thin and pale, however eat-13 is less sensitive to PA14 than esp-1 (see below FIG. 3) and eat-13 complements esp-1 for both the Eat and Esp phenotypes.

esp-1 Phenotype is Correlated with a Grinder Abnormality

Since all of the characterized feeding defective mutants have abnormalities in either pharyngeal structure or the motion of the pharynx, the pharyngeal pumping of esp-1 was examined under Nomarski optics. The nematode feeding cycle has a number of well defined steps (muscle contractions and relaxations) that are required to ingest bacteria, move the bacteria through the pharynx, grind the bacteria, and expel any liquid taken up with the bacteria (Avery, *Genetics* 133: 897–917, 1993).

Figure 3:
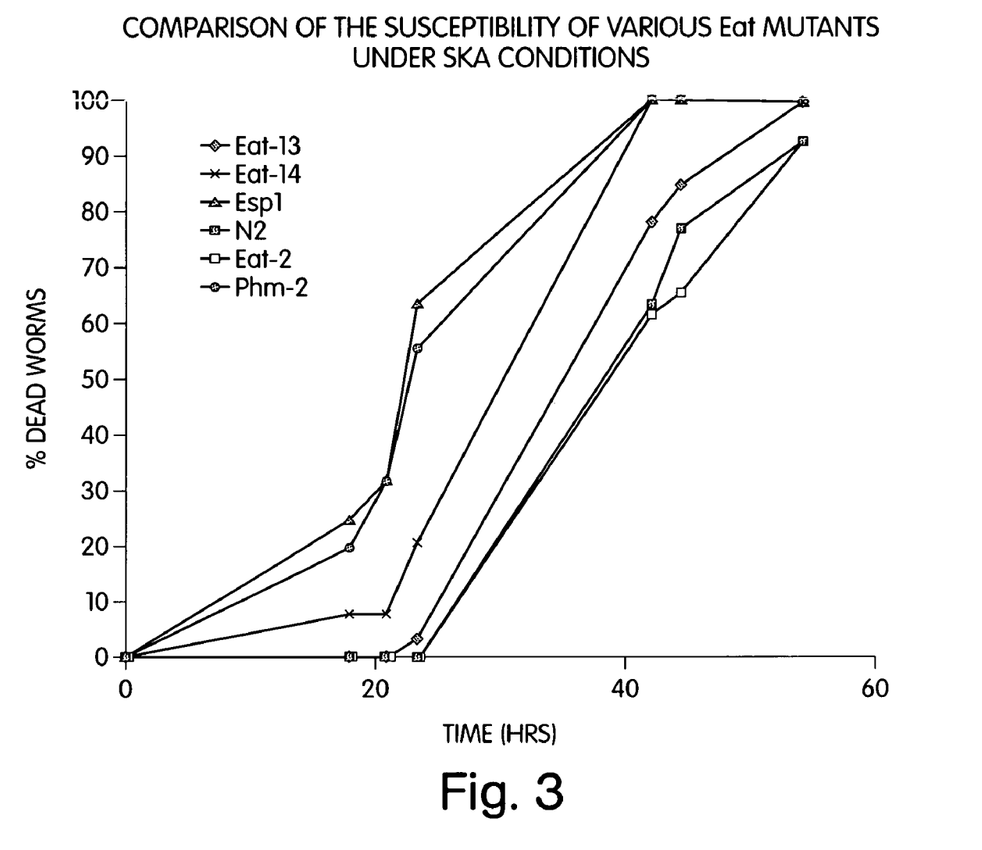
FIG. 3 is a graph showing a comparison of the susceptibility of various Eat mutants and N2 under SKA (slow killing assay) conditions.
Figure 4:
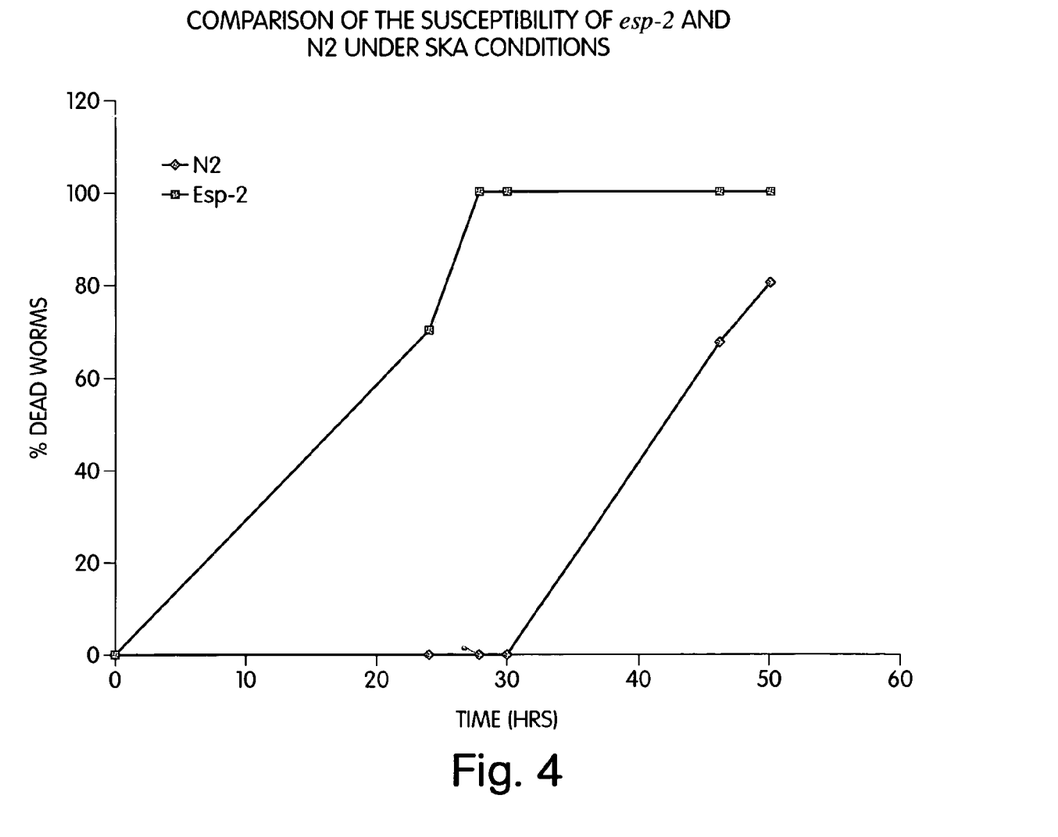
FIG. 4 is a graph showing a comparison of the susceptibility of esp-2 and N2 under SKA conditions.

In esp-1, the movement of the grinder is abnormal; grinder function is necessary for breaking up bacteria before they enter the intestine. This observation suggested that the esp-1 mutant was more susceptible to PA14 because of an increased entry of live bacteria into the gut. To test this hypothesis, the susceptibility of various eating defective mutants to PA14 was tested. The slow pumping mutant (eat-2) and mutants either strongly (phm-2) or slightly (eat-13, eat-14) defective in the grinder motion were compared with esp-1. Only mutants with grinding defects exhibited an enhanced susceptibility to PA14, with the degree of sensitivity correlating with the severity of the grinding defect (FIG. 3). In agreement with these results, the eat-2 mutant which pumps slowly but has a normal grinder function, is not sensitive to PA14 under slow killing conditions.

Bacteria are Able to Colonize Rapidly the esp-1 Gut

To determine whether the grinder defect in esp-1 results in an abnormally large number of live bacteria entering the gut, worms were fed bacteria containing a GFP-expressing plasmid (Tan et al., *Proc. Natl. Acad. Sci.* 96: L715–720, 1999). In the case of the wild type N2 strain, 2 hours of feeding on GFP expressing PA14 results in a lumen of a diffuse green color without intact bacteria. After the same period of time, the lumen of the esp-1 mutant was filled with live, glowing, green bacteria. These results suggest that the ingested bacteria were able to colonize and proliferate in the esp-1 gut.

Our analysis of esp-1 further suggests that it represents a previously unidentified feeding defective mutant and that its enhanced susceptibility to PA14 is at least in part a consequence of large numbers of live bacteria entering the gut. The possibility that the esp-1 mutation has additional effects that favor bacterial colonization and infection has not been ruled out.

Characterization of esp-2 and esp-8

The mutant designated esp-2 was characterized according to standard methods. After backcrossing the esp-2 mutant, over 70% of esp-2 young adult animals were dead after only 24 hours on PA14 under SKA conditions (FIG. 3). esp-2 was also found to be sensitive to the gram positive pathogen *Enterococcus faecalis*. In addition, esp-2 animals are somewhat Egl (egg laying defective). Preliminary experiments have shown that approximately 10% of esp-2 young adults bag after 24 hours on *E. coli*, and the number of bagging animals was found to increase to approximately 30% after 48 hours. In addition, the number of eggs laid over a 48 hour period at 20° C., by esp-2 animals that do not bag is reduced as compared to N2. However, the sensitivity of esp-2 to PA14 is not merely due to the Egl defect because esp-2 males were also found to be sensitive to PA14. esp-2 males may be defective in mating; although esp-2 males can be generated by heat shock, several attempts at establishing a male mating stock have failed.

In order to establish the sensitivity of esp-2 hermaphrodites to PA14 in the absence of any contribution of the Egl defect, double mutants of esp-2 and esp-8 with the temperature sensitive sterile glp-4 mutant were constructed. The glp-4 mutation alone extended the viability of worms on PA14 ($LT_{50}$=72 hours). A subset of glp-4 mutant animals also remained alive for an extended period of time on PA14. This mirrored an overall extension of lifespan in a subpopulation of glp-4 animals. However, esp-2; glp-4 and esp-8; glp-4 hermaphrodites showed enhanced susceptibility to PA14 ($LT_{50}$=30 hours).

To identify mutants with an enhanced susceptibility to pathogens, mutants with non-specific defects in overall health were identified. As an indication of overall health the lifespan of esp-2 and esp-8 animals was determined. Lifespan was assayed on plates containing FUDR, a compound that prevents the generation of progeny. The lifespans of esp-2 and esp-8 worms were not significantly different from those of wild-type worms. Furthermore, esp-2 and esp-8 worms developed and reached adulthood concomitant with wild-type worms.

Bacteria Rapidly Colonize the esp-2 and esp-8 Gut

Paralleling the enhanced susceptibility of esp-2 and esp-8 mutants to PA14 is a rapid accumulation of PA14 in the intestine of these mutants. esp-2 and esp-8 mutants fed GFP labeled PA14 accumulated visible levels of GFP PA14 bacteria in their intestine after 22 hours, when only trace amounts were observed in the gut of wild-type worms. The most anterior portion of the intestine is the first region to show accumulation of GFP PA14. The rapid accumulation of GFP PA14 bacteria within the intestine of esp-2 and esp-8 worms was not due to constipation or defects in the ability of the worms to grind food. Both esp-2 and esp-8 have normal defecation cycles, are not Eat, and have no observable defect in pharynx action.

Mapping of esp-2 and esp-8

For esp-2 and esp-8 mutants we have utilized the recently developed mapping strain CB4856 that contains a large number of single nucleotide polymorphisms or SNPs (Wicks et al., *WBG* 16(1): 28; see also the *C. elegans* SNP index at the Genome Sequencing Center website at Washington University at St. Louis. Many snip-SNP markers, that are detected by a restriction digest, have been identified from CB4856. CB4856 has several advantages over RW7000 as a mapping strain, there are more SNP markers than TC1 markers for use in mapping and the SNP markers permit the detection of both the CB4856 and the N2 allele. We crossed CB4856 males to esp-2 and picked approximately 1,000 F2 hermaphrodite cross progeny directly to SKA plates. After 24 hours on PA14 SKA plates, over 200 dead animals were singly placed onto *E. coli* plates, with the assumption that these would be esp-2/esp-2 animals. 130 of the dead animals yielded progeny. The esp-2/esp-2 plates were allowed to starve, the worms were washed from the plate, and DNA was prepared from these worms according to standard methods. All of the original plates were saved, so that it was then possible to verify the Esp phenotype of each F2 picked (this was done for 20% of the strains, all critical recombinants were rigorously tested for their Esp phenotype).

Using the available snip-SNP markers, esp-2 was mapped to a 0.3 map unit region left of center on the X chromosome. There are no other previously identified Esp genes in this interval. The esp-2 interval was also examined using the available *C. elegans* genetic map and sequence data. Candidate open reading frames within this interval were sequenced, including the sek-1 open reading frame (ORF) that encodes a homolog of the MKK3/MKK6 type map kinase kinase (MAPKK). A single base pair change, G212R, was found within the sek-1 ORF. Microinjection of a 9.25 kb fragment containing the sek-1 open reading frame rescued both the Esp and Egl phenotypes of esp-2. In addition, a sek-1 deletion allele that removes kinase domains II–XI of SEK-1 showed enhanced susceptibility to PA14. These results indicate that esp-2 is sek-1. The wild type sequences of the sek-1 mRNA and SEK-1 amino acid sequences are found in Genbank, accession numbers AB060731 and BAB43977, respectively.

Using standard snip-SNP markers, esp-8 was mapped to a 500 kb region of chromosome II. In addition, the esp-8 interval was examined using the available *C. elegans* genetic map and sequence data. Within this interval, the SEK-1 activator nsy-1, a map kinase kinase kinase (MAPKKK) was identified. Sequencing of the esp-8 allele revealed an early stop codon at position 1013 in nsy-1. Microinjection of a genomic fragment containing the nsy-1 ORF and 3.8 kb of upstream promoter rescued the Esp and Egl phenotypes of esp-8. These results indicated that esp-8 is nsy-1. Accordingly, *C. elegans* nsy-1 encodes a homologue of the human MAPKKK, ASK1, the apoptosis signal-regulating kinase, an activator of p38 and JNK. The wild type amino acid sequence of esp-8 is shown in Sagasti et al., *Cell* (2001) 105: 221–232 and the genomic sequence is included in cosmid F59A6.1 (GenBank accession number U41994).

nsy-1 and sek-1 Function in a Map Kinase Signaling Cascade

The nsy-1 and sek-1 genes have been shown to function in a map kinase signaling cascade that controls a lateral signaling decision in the AWC olfactory neurons. The nsy-1 gene was isolated in a screen for Neuronal Symmetry mutants. These mutants express the olfactory receptor, str-2, symmetrically in each of the two bilaterally symmetric AWC olfactory neurons, rather than asymmetrically in only one of the two AWC neurons as wild-type worms do. Two alleles of nsy-1(ky397) and nsy-1(ky400) were identified in a screen for Nsy mutants. These alleles were tested for the Esp phenotype. Both ky397 and ky400, nonsense mutations in nsy-1, were sensitive to PA14. In addition, a deletion allele sek-1(km4) that removed SEK-I kinase domains II-XI was also tested. The km4 allele was generated using a standard transposon-based mutagenesis method. Like nsy-1, sek-1 (km4) expressed the str-2 odor receptor in both AWC neurons and showed enhanced susceptibility to PA14. Based on these data the nsy-1/sek-1 map kinase signaling cascade was found to play a role in defense against pathogens.

NSY-1/SEK-1 Acts Through p38 Map Kinase to Fight Bacterial Infections

The MKK3/MKK6 MAPKKs are specific activators of p38 map kinases in other organisms. C. elegans SEK-1 was shown to phosphorylate mammalian p38 in vitro. Two p38 map kinases pmk-1 and pmk-2, were identified in C. elegans. pmk-1 and pmk-2 are arranged in an operon. A deletion mutant of pmk-2, which is the first gene in the operon, was found to be non-viable. No deletion in pmk-1 is available. To address whether p38 might play a role in the response to pathogens, pmk-1 gene activity was inhibited by RNAi. Wild-type L1 larval animals were synchronized by hatching overnight in M9, then dropped onto RNAi feeding plates spread with bacteria containing either a pmk-1 RNAi vector or the RNAi vector without insert. Worms were grown until the L4 stage on the RNAi bacterial lawn and then washed off in M9 and dropped onto PA14. pmk-1 RNAi resulted in enhanced susceptibility to PA14. At 27 hours after exposure to PA14 only 37% of the pmk-1 RNAi animals were alive. At 32 hours none of the pmk-1 RNAi worms was alive, while 80% of the control group were still living. pmk-1 is found on cosmid B0218.3 (Genbank accession number U58752), and the amino acid sequence of the PMK-1 protein is found in GenBank (accession number AAB00664).

UNC-43 CaMKII, An Upstream Activator of nsy-1 in Signaling Neuronal Fates Does not Play a Role in the Response to Pathogens C. elegans unc-43 encodes CaMKII. unc-43 was found to be expressed in many cells that also express nsy-1, including neurons, muscle and intestine. unc-43 loss-of-function (lf) mutants expressed str-2 in both AWC neurons, as nsy-1(lf) mutants did. unc-43 gain-of-function (gf) mutants had the opposite phenotype, expressing str-2 in neither AWC. Epistasis analysis indicated that nsy-1 is genetically downstream of unc-43. In addition, C. elegans CaMKII/UNC-43 was found to associate with NSY-1/MAPKKK in heterologous cells. This indicated that UNC-43 activated the NSY-1 signaling cassette to execute a signal required for asymmetric olfactory neuron fate.

To test whether unc-43 was also required to activate nsy-1 in response to pathogens, several unc-43 mutants response to PA14 was tested under slow killing conditions. The unc-43(lf) mutants showed no or little enhanced susceptibility to PA14, suggesting that CaMKII does not activate nsy-1 in response to pathogens. In contrast, unc-43(gf) mutants died more rapidly than wild-type worms did when exposed to PA14. This susceptibility was most likely due to the constipation phenotype of unc-43(gf). It was previously observed that mutants defective in the expulsion step of the defecation motor program had an enhanced susceptibility to PA14, presumably due to their reduced ability to clear the pathogenic bacteria from the gut. The observation that unc-43(lf) mutants died concomitantly with wild-type worms when exposed to PA14 implies that calcium may not be a primary signal in activation of the nsy-1 map kinase signaling cassette in response to pathogens and distinguishes the pathogenic signaling pathway from that of neuronal differentiation.

Saturation Screen for C. elegans Mutants that are Sensitive to Infection Mediated Killing by PA14

Using the above-described methods, a large collection of C. elegans mutants having enhanced susceptibility to pathogen infection mediated killing is readily generated. Such mutants are then used to define the molecular pathways and host pathogen defense responses utilized by C. elegans to combat infection.

Mutants identified using these screens may then be characterized and categorized as follows. (1) Mutants are tested for growth on E. coli, and only mutants showing premature death on PA14, but not on E. coli are selected for detailed characterization. (2) Highly penetrant mutants that segregate as a single locus in standard backcrossing experiments are also selected for detailed characterization. (3) Mutants showing either a (i) constipated phenotype on E. coli, or (ii) eating defect, particularly a grinding defect, are generally not of immediate interest. The constipated phenotype is easily scored under the dissecting microscope and eating defective mutants generally appear thin and somewhat starved. All eating defective mutants are screened for an aberration in the action of the grinder by observation under Nomarski optics. (4) Additional pathogens that kill C. elegans are also useful for analyzing host response, such pathogens include the gram positive Enterococcus faecalis and Salmonella typhimurium. Mutants showing an enhanced sensitivity to a plurality of pathogens are especially useful, e.g., mutants having enhanced susceptibility to PA14, Enterococcus, and Salmonella. To avoid mutants that are merely compromised in their health, mutants that are sensitive to two but not all three pathogens are also useful.

Mutants selected using the above-mentioned guidelines are further analyzed. For example, a mutant may be placed into a class based on the pattern and kinetics of accumulation of PA14 in the gut. This analysis is useful for further characterizing the mutant phenotype; determining whether more live bacteria are entering the gut, and whether the PA14 proliferate more rapidly in a given Esp mutant or to a higher titer. The profile of accumulation of PA14 in the gut is generally examined in two ways. A GFP carrying PA14 strain is used to follow the accumulation of bacteria in the gut of the various C. elegans Esp mutants by direct observation under the UV microscope. In addition, the number of live bacteria in the gut is quantitated using pulse/chase experiments involving feeding the C. elegans mutants PA14 for a short amount of time, grinding up the worms to recover live bacteria, and counting the bacteria after plating on the appropriate media.

Esp mutants may also be categorized based on their sensitivity to PA14 having mutations in known virulence factors. There are currently 23 PA14 mutants that have been shown to be attenuated in the C. elegans slow killing assay and more are continually being identified. To identify C. elegans host pathogen defense genes that respond to particular virulence factors or groups of virulence factors, mutant worms are tested against PA14 mutants in known virulence factors whose role in pathogenesis is well defined and conserved across multi-host systems.

Esp mutants may also be classified based on their expression of C. elegans pathogen regulated genes. To identify pathogen regulated genes in C. elegans, worms exposed to pathogens, and RNA is extracted from the nematodes over the time course of infection. This RNA will be then used to hybridize to DNA microarrays. The expression of genes that are identified as pathogen regulated will be examined in the various mutant backgrounds in order to place the Esp mutants in a regulatory hierarchy.

Cloning of C. elegans Esp Genes

Using the CB4856 mapping strain, map positions for a large number of C. elegans Esp mutants are routinely obtained, and such mutants may be mapped using standard techniques to a several map unit interval. Candidate Esp genes for cloning are those that present strong phenotypes and fall into the exemplary classes described above. In order to clone putative Esp genes, it is necessary to obtain a fine map position (on the order of 0.2–0.5 map units), and to obtain informative recombinants to define a small genetic interval. The phenotype of each recombinant (e.g., it has been observed that even for very strong Esp mutants up to 10% of the animals picked in the mapping experiments as esp/esp are in fact either heterozygous or homozygous for the CB4856 chromosome) is carefully verified. Continued mapping with physical markers using CB4856 and classical mapping with applicable visual markers is useful to obtain a fine map position for Esp genes of interest. Once a particular Esp gene is delimited to a small region, cloning is accomplished using a variety of methods such as microinjection rescue with cosmid pools and direct sequencing (Mello et al., EMBO 10:3959–3970, 1991). Since many of the Esp mutants have pleiotropic phenotypes, this information is useful for identifying candidate genes corresponding to an Esp genes. Candidate genes are then tested to determine whether they correspond to an Esp gene using such standard methods as microinjection rescue or complementation tests (if mutants already exist in the candidate).

For example, fine mapping, cosmid rescue, and DNA sequencing revealed that the esp-1 mutation was in the troponin T gene.

Alternative Methods to the Identification of Host Defense Genes in C. elegans

In addition to the traditional methods of mutagenesis and gene cloning described above, RNA-mediated interference (RNAi) technology (Fire et al., Nature 391: 806–811, 1998), in which sequence-specific silencing of genes is accomplished by introduction into the worm of double-stranded RNA (dsRNA), is utilized to identify genes involved in the C. elegans response to pathogens. Candidate genes identified through sequence analysis of the C. elegans genome are tested for their role in pathogen susceptibility by silencing genes of the nematode using either microinjection of dsRNA or feeding of worms with bacteria that are expressing dsRNA. A synchronized population of L4 N2 (wild-type) nematodes is either microinjected with dsRNA that has been synthesized from an in vitro transcription reaction or fed an E. coli strain that has been engineered to produce dsRNA. The progeny of the exposed L4 worms are subsequently grown to the L4 stage and assayed for enhanced susceptibility to a pathogen (e.g., P. aeruginosa or E. faecalis) using the slow-killing protocols described above. The sequence of the dsRNA dictates the specific gene being silenced, and an alteration in the susceptibility of the worm to killing may be attributed to the loss of function of the silenced gene.

Furthermore, genes involved in C. elegans host defense are identified using genome-wide screening RNAi methodology (Fraser et al., Nature 408: 325–330, 2000; Gonczey et al., Nature 408: 331–336, 2000). C. elegans worms are injected with dsRNA or fed bacteria expressing dsRNA corresponding to individual genes targeted for gene silencing, then subjected to exposure to a pathogen. The sequence of the injected or ingested dsRNA effecting increased susceptibility of the nematode to the pathogen provides the identity of the gene that has been affected, indicating a role in the host response.

For example, a library of bacteria engineered to express dsRNA corresponding to individual specific clones (e.g., C. elegans genes) is constructed by standard methods. Subsequently, L4 worms are placed on the library of bacteria as a food source. The progeny of these worms are continually grown on the dsRNA-expressing bacteria according to Fraser et al. (Nature 408: 325–330, 2000) until the L4 stage, at which point a pathogen is added to the food source, or alternatively, the worms are then transferred to a plate with pathogen for further assay. Performed in a systematic manner, the C. elegans genome is screened for all genes that confer increased susceptibility to pathogen when silenced by RNAi.

MapK Signaling Cascades and Identification of Innate Immunity Genes in C. elegans As discussed above, the identification of esp-2, esp-8, and pmk-1 highlighted the importance of MapK signal transduction in generating a C. elegans host defense response. Accordingly, the identification of a MapK signal transduction cascade facilitates the isolation of additional C. elegans innate immunity genes encoding components of the MAPK signaling pathway. Genes identified as components of the C. elegans MAPK signal cascade may have mammalian homologues that have not yet been identified in the mammalian innate immunity response.

To identify additional C. elegans innate immunity genes, the C. elegans genome sequence is analysed for additional members of MAPK signaling cascades. Exemplary genes of the MapK signal transduction pathway include MAPKKKs, MAPKKs, and MAPKs. C. elegans homologues of p38 (three p38 homologues in C. elegans), jnk-1 map kinases and their upstream activating MAPKK's and MAPKKKs are useful in the methods of the invention. The role of the MAPKKK, MAPKK, or MAPK in innate immunity is then tested using the methods described herein. For example, the MAPK, jnk-1, is targeted for deletion or inactivation, for example, by RNAi using standard methods. Deletions are isolated using a PCR-based screen of a chemically mutagenized worm library. The deletion mutants or RNAi containing worms are then characterized for Esp using methods described herein. Worms expressing an attenuated MapK signal transduction pathway that are susceptible to pathogen infection are taken as useful in the invention.

In addition, forward genetic screens are performed in sensitized backgrounds to identify additional components of MAPK signaling pathways. esp-2 worms, for example, are mutagenized according to standard methods and mutant worms are then identified that either suppress or enhance the esp-2 PA14 sensitivity phenotype. Such mutants are then used to define the MAPK pathways and host pathogen defense responses utilized by C. elegans to combat infection. Mutants identified using these screens may then be characterized and categorized as previously described.

Compound Screening Assays

As discussed above, our experimental results demonstrated that mutations in host pathogen defense genes, e.g., esp-1, esp-2, esp-8, or pmk-1 render the nematode, C. elegans, more susceptible to pathogen infection. Based on this discovery we have also developed a screening procedure for identifying therapeutic compounds (e.g., drugs) which can be used to promote or enhance the ability of a host to combat pathogen infection, block pathogen virulence, or both. In general, the method involves screening any number of compounds for therapeutically-active agents by employing the pathogen/nematode killing system (e.g., the PA14/C. elegans slow killing assay) described herein. Based on our demonstration that mutant C. elegans are more susceptible to PA14 and E. faecalis, e.g., the Esp mutants described herein, it will be readily understood that a compound which promotes a host's defense response provides an effective therapeutic agent in a mammal (e.g., a human patient). Since the screening procedures of the invention are performed in vivo, it is also unlikely that the identified compounds will be highly toxic to the host organism.

In general, the chemical screening methods of the invention provide a straightforward means for selecting natural product extracts or compounds of interest from a large population which are further evaluated and condensed to a few active and selective materials. Constituents of this pool are then purified and evaluated in the methods of the invention to determine their anti-pathogenic activity.

Test Extracts and Compounds

In general, novel anti-pathogenic drugs are identified from large libraries of both natural product or synthetic (or semi-synthetic) extracts or chemical libraries according to methods known in the art. The screening method of the present invention is appropriate and useful for testing compounds from a variety of sources for possible anti-pathogenic activity. The initial screens may be performed using a diverse library of compounds, but the method is suitable for a variety of other compounds and compound libraries. Such compound libraries can be combinatorial libraries, natural product libraries, or other small molecule libraries. In addition, compounds from commercial sources can be tested, as well as commercially available analogs of identified inhibitors.

For example, those skilled in the field of drug discovery and development will understand that the precise source of test extracts or compounds is not critical to the screening procedure(s) of the invention. Accordingly, virtually any number of chemical extracts or compounds can be screened using the methods described herein. Examples of such extracts or compounds include, but are not limited to, plant-, fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

In addition, those skilled in the art of drug discovery and development readily understand that methods for dereplication (e.g., taxonomic dereplication, biological dereplication, and chemical dereplication, or any combination thereof) or the elimination of replicates or repeats of materials already known for their anti-pathogenic activity should be employed whenever possible.

When a crude extract is found to have activity that promotes or enhances a host's defense to a pathogen, further fractionation of the positive lead extract is necessary to isolate chemical constituents responsible for the observed effect. Thus, the goal of the extraction, fractionation, and purification process is the careful characterization and identification of a chemical entity within the crude extract having anti-pathogenic activity. Methods of fractionation and purification of such heterogenous extracts are known in the art. If desired, compounds shown to be useful agents for the promoting or enhancing a host defense response are chemically modified according to methods known in the art.

Since many of the compounds in libraries such as combinatorial and natural products libraries, as well as in natural products preparations, are not characterized, the screening methods of this invention provide novel compounds which are active as inhibitors or inducers in the particular screens, in addition to identifying known compounds which are active in the screens. Therefore, this invention includes such novel compounds, as well as the use of both novel and known compounds in pharmaceutical compositions and methods of treating.

There now follows examples of high-throughput systems useful for evaluating the efficacy of a molecule or compound in promoting or enhancing a host's resistance to a pathogen. These examples are provided to illustrate, not limit, the invention.

Exemplary High Throughput Screening Systems

To evaluate the efficacy of a molecule or compound in promoting host resistance to, or inhibiting pathogenicity of a pathogen, a number of high throughput assays may be utilized.

For example, to enable mass screening of large quantities of natural products, extracts, or compounds in an efficient and systematic fashion *Caenorhabditis elegans* (e.g., esp-1 or esp-2, or esp-8 or strains that include dsRNA, such as pmk-1, as described herein) are cultured in wells of a microtiter plate, facilitating the semiautomation of manipulations and full automation of data collection. As is discussed above, bacterial pathogens kill *C. elegans* under slow killing conditions and worms having enhanced susceptibility to such pathogens are readily isolated.

To evaluate the ability of a test compound or extract to promote a host's resistance to a pathogen or to repress pathogenicity of a pathogen, a test compound or extract is inoculated at an appropriate dosage into an appropriate agar medium seeded with an appropriate amount of an overnight culture of a pathogen, e.g., *S. typhimurium* strain LT2 or PA14. If desired, various concentrations of the test compound or extract can be inoculated to assess dosage effect on both the host worm and the pathogen. Worms having enhanced susceptibility to a pathogen are engineered and identified as described herein. Control wells are inoculated with non-mutated worms (negative control) or a mutated worm in the absence of a test compound or extract positive control) or worms lacking dsRNA. Plates are inoculated with the pathogen and then incubated 24 hours at 37° C. to facilitate the growth of the pathogen. Microtiter dishes are subsequently cooled to 25° C., and two *C. elegans* L4 hermaphrodites (either mutant or wild type) expressing a detectable marker such as GFP are added to the plate and incubated at 25° C., the upper limit for normal physiological integrity of *C. elegans*. At an appropriate time interval, e.g., 24 hours, wells are examined for surviving worms, the presence of progeny, or both, e.g., by visual screening or monitoring motion of worms using a motion detector, or monitoring the fluorescence of the nematodes.

Comparative studies between treated and control worms (or larvae) are used to determine the relative efficacy of the test molecule or compound in promoting the host's resistance to the pathogen or inhibiting the establishment of a persistent infection. A test compound which effectively stimulates, boosts, enhances, increases, or promotes the host's resistance to the pathogen or which inhibits, inactivates, suppresses, represses, or controls pathogenicity of the pathogen, and does not significantly adversely affect the normal physiology, reproduction, or development of the worms is considered useful in the invention.

Use

The methods of the invention provide a simple means for identifying host factors and genes that enable a host to combat pathogen infection and compounds capable of either inhibiting pathogenicity or enhancing a host's resistance capabilities to such pathogens. Accordingly, a chemical entity discovered to have medicinal value using the methods described herein are useful as either drugs, or as information for structural modification of existing anti-pathogenic compounds, e.g., by rational drug design.

For therapeutic uses, the compositions or agents identified using the methods disclosed herein may be administered systemically, for example, formulated in a pharmaceutically-acceptable buffer such as physiological saline. Preferable routes of administration include, for example, subcutaneous, intravenous, interperitoneally, intramuscular, or intradermal injections which provide continuous, sustained levels of the drug in the patient. Treatment of human patients or other animals will be carried out using a therapeutically effective amount of an anti-pathogenic agent in a physiologically-acceptable carrier. In the context of treating a bacterial infection a "therapeutically effective amount" or "pharmaceutically effective amount" indicates an amount of an antibacterial agent, e.g., as disclosed for this invention, which has a therapeutic effect. This generally refers to the inhibition, to some extent, of the normal cellular functioning of bacterial cells causing or contributing to a bacterial infection. The dose of antibacterial agent which is useful as a treatment is a "therapeutically effective amount." Thus, as used herein, a therapeutically effective amount means an amount of an antibacterial agent which produces the desired therapeutic effect as judged by clinical trial results, standard animal models of infection, or both. This amount can be routinely determined by one skilled in the art and will vary depending upon several factors, such as the particular bacterial strain involved and the particular antibacterial agent used. This amount can further depend on the patient's height, weight, sex, age, and renal and liver function or other medical history. For these purposes, a therapeutic effect is one which relieves to some extent one or more of the symptoms of the infection and includes curing an infection.

The compositions containing antibacterial agents of virulence factors or genes can be administered for prophylactic or therapeutic treatments, or both. In therapeutic applications, the compositions are administered to a patient already suffering from an infection from bacteria (similarly for infections by other microbes), in an amount sufficient to cure or at least partially arrest the symptoms of the infection. An amount adequate to accomplish this is defined as "therapeutically effective amount." Amounts effective for this use will depend on the severity and course of the infection, previous therapy, the patient's health status and response to the drugs, and the judgment of the treating physician. In prophylactic applications, compositions containing the compounds of the invention are administered to a patient susceptible to, or otherwise at risk of, a particular infection. Such an amount is defined to be a "prophylactically effective amount." In this use, the precise amounts again depend on the patient's state of health, weight, and the like. However, generally, a suitable effective dose will be in the range of 0.1 to 10000 milligrams (mg) per recipient per day, preferably in the range of 10–5000 mg per day. The desired dosage is preferably presented in one, two, three, four, or more subdoses administered at appropriate intervals throughout the day. These subdoses can be administered as unit dosage forms, for example, containing 5 to 1000 mg, preferably 10 to 100 mg of active ingredient per unit dosage form. Preferably, the compounds of the invention will be administered in amounts of between about 2.0 mg/kg to 25 mg/kg of patient body weight, between about one to four times per day.

Suitable carriers and their formulation are described, for example, in Remington's *Pharmaceutical Sciences* by E. W. Martin. The amount of the anti-pathogenic agent to be administered varies depending upon the manner of administration, the age and body weight of the patient, and with the type of disease and extensiveness of the disease. Generally, amounts will be in the range of those used for other agents used in the treatment of other microbial diseases, although in certain instances lower amounts will be needed because of the increased specificity of the compound. A compound is administered at a dosage that inhibits microbial proliferation.

All publications and patents mentioned in this specification are herein incorporated by reference to the same extent as if each individual publication or patent was specifically and individually indicated to be incorporated by reference.

From the foregoing description, one skilled in the art can easily ascertain the essential characteristics of this invention, can make various changes and modifications of the invention to adapt it to various usages and conditions. Thus, other embodiments are also within the claims.

What is claimed is:

1. A method for identifying a nematode having enhanced susceptibility to a pathogen, said method comprising the steps of:
    (a) exposing a mutagenized nematode comprising a mutation in a component of a mitogen-activated protein kinase (MAPK) signal transduction pathway to a pathogen; and
    (b) determining survival of said mutagenized nematode when exposed to said pathogen, decreased survival of said mutagenized nematode relative to a non-mutagenized nematode identifying said mutagenized nematode as one having enhanced susceptibility to the pathogen.

2. The method of claim 1, wherein said component of the MAPK signal transduction pathway is esp-2.

3. The method of claim 1, wherein said component of the MAPK signal transduction pathway is esp-8.

4. The method of claim 1, wherein said component of the MAPK signal transduction pathway is pmk-1.

5. The method of claim 1, wherein said mutagenized nematode is *C. elegans*.

6. The method of claim 5, wherein said *C. elegans* is an N2 L4 worm.

7. The method of claim 1, wherein said pathogen is a bacterium.

8. The method of claim 7, wherein said bacterium is *Pseudomonas aeruginosa* (strain PA14).

9. The method of claim 7, wherein said bacterium is *Enterococcus faecalis*.

10. The method of claim 1, wherein said mutagenized nematode is exposed to said pathogen under slow killing conditions.

11. A method for identifying a pathogen defense response gene, said method comprising the steps of:
(a) exposing a mutagenized nematode comprising a mutation in a component of a MAPK signal transduction pathway to a pathogen;
(b) determining survival of said mutagenized nematode when exposed to said pathogen, decreased survival of said mutagenized nematode relative to a non-mutagenized nematode indicating a mutation in a nematode pathogen defense response gene; and
(c) using said mutation as a marker for identifying said pathogen defense response gene.

12. The method of claim 11, wherein said component of the MAPK signal transduction pathway is esp-2.

13. The method of claim 11, wherein said component of the MAPK signal transduction pathway is esp-8.

14. The method of claim 11, wherein said component of the MAPK signal transduction pathway is pmk-1.

15. The method of claim 11, wherein said mutagenized nematode is *C. elegans*.

16. The method of claim 15, wherein said *C. elegans* is an N2 L4 worm.

17. The method of claim 11, wherein said pathogen is a bacterium.

18. The method of claim 17, wherein said bacterium is *Pseudomonas aeruginosa* (strain PA14).

19. The method of claim 17, wherein said bacterium is *Enterococcus faecalis*.

20. The method of claim 11, wherein said mutagenized nematode is exposed to said pathogen under slow killing conditions.

* * * * *